United States Patent [19]

Grunwald

[11] 4,309,994
[45] Jan. 12, 1982

[54] CARDIOVASCULAR CANNULA

[76] Inventor: Ronald P. Grunwald, W. 801 - 5th Ave., Spokane, Wash. 99204

[21] Appl. No.: 124,335

[22] Filed: Feb. 25, 1980

[51] Int. Cl.³ .................. A61M 5/00; A61M 25/00
[52] U.S. Cl. .............................. 128/214 R; 128/348; 128/350 R
[58] Field of Search ............... 128/214 R, 214.4, 345, 128/130, 131, 348–350, 207.15

[56] References Cited

U.S. PATENT DOCUMENTS

| | | | |
|---|---|---|---|
| 945,741 | 1/1910 | Birkenkamp | 128/345 X |
| 2,624,341 | 1/1953 | Wallace | 128/350 R |
| 2,935,068 | 5/1960 | Donaldson | 128/348 |
| 3,460,541 | 8/1969 | Doherty | 128/207.15 |
| 3,835,863 | 9/1974 | Goldberg et al. | 128/350 R |
| 3,903,895 | 9/1975 | Alley et al. | 128/350 R |
| 4,114,618 | 9/1978 | Vargas | 128/214.4 |
| 4,129,129 | 12/1978 | Amrine | 128/214 R |
| 4,248,224 | 2/1981 | Jones | 128/214 R |

Primary Examiner—Dalton L. Truluck
Attorney, Agent, or Firm—Wells, St. John & Roberts

[57] ABSTRACT

A bifurcated venous return cannula assembly is described for insertion into the vena cavae through a single incision in the right atrium. The cannula includes a single outward tube that is bifurcated at an inward end, forming two normally diverging flexible branches. The tube branches diverge naturally from the central axis of the single tube. An obturator slidably engages the bifurcated end of the tube to hold the branches together along the tube axis during initial insertion and to draw the branches back together within the atrium upon withdrawal. The obturator also enables the branch ends to separate within the atrium following initial insertion. The separating tube ends seek out and ascend the superior vena cava, and descend the inferior vena cava due to the natural resiliency of the branches and their tendency to seek their normal diverging positions.

6 Claims, 9 Drawing Figures

CARDIOVASCULAR CANNULA

BACKGROUND OF THE INVENTION

The present invention is related to venous return cannulas for cardiopulmonary bypass to an extracorporeal heart-lung circuit.

In most cardiopulmonary bypass techniques, the preferred area of insertion for the venous return cannula is the appendix of the right atrium. The auricular appendix is convenient for clamping purposes and is conveniently located for cannulation. In fact, the auricular appendix has at times been referred to as "God's gift to the heart surgeon".

Many forms of cardiopulmonary bypass techniques involve the use of more than one venous return line. The appendix can accept only one cannula while the other must be inserted through an incision made elsewhere in the atrium. The double incision requires placement of two separate sutures for snaring the cannulas after insertion. All this preparation takes valuable time and increases the chances for later complication. The two cannulas interfere with critical surgical procedures and in doing so, further increase the overall time required to complete the surgery.

It becomes desirable, since the venous drainage cannulas lead into the same phlebotomy line of the extracorporeal circuit, to use a single cannula inserted through a single incision in the atrium appendix. This has not been possible, however, because it often becomes necessary to clamp or "tape" the inferior and superior vena cavae about the cannulas, preventing flow of blood into the right atrium. The physical separation of the vena cavae prohibit such practice with a single tubular cannula.

The typical double cannula arrangement is shown in U.S. Pat. No. 3,903,895 to R. D. Alley et al. FIG. 4 of Alley's drawings show a venous return line of an extracorporeal circuit with a double tubular end, one cannula end is inserted through an incision in the atrium and is extended upwardly into the superior vena cava (SVC). The remaining cannula is inserted through a second, separate incision and is directed downwardly into the inferior vena cava (IVC). The two branches extend outwardly of the heart to connect with converging lines of the extracorporeal heart-lung circuit.

An infusion cannula is typically inserted into the aorta, further obstructing the operative area. The three protruding tubes, though flexible, hinder positioning of the heart to facilitate aortocoronary bypasses, valve implants, etc. In addition, the three tubes hinder direct access by the various surgical instruments used in such heart operations.

U.S. Pat. No. 3,835,863 to Goldberg et al discloses a "T" tube that is used as a catheter for implantation in an internal duct for drainage. The transverse arms of the "T" tube are slotted longitudinally to enable folding over one another to the diameter of the main tube branch. The tubes can thus be folded onto one another and inserted through an incision in the associated duct. Upon insertion, the tube branches may spring apart, opening into the duct. Withdrawal of the tube is accomplished simply by pulling the tube outwardly. The transverse branches of the tube will fold together at the incision as the tube is pulled outwardly.

The Goldberg "T" tube may have beneficial use in drainage of internal ducts such as the bile ducts in abdominal surgery. However, such a drainage tube would not be functional for use as a venous return cannula, due to the open slots formed along the tube branches. Furthermore, the open tubes would not lend themselves to operation with an inside or outside obturator by which the branch ends could be accurately guided as they are inserted or withdrawn from the incision.

DETAILED DESCRIPTION OF THE PREFERRED EMBODIMENT

Figure 1:
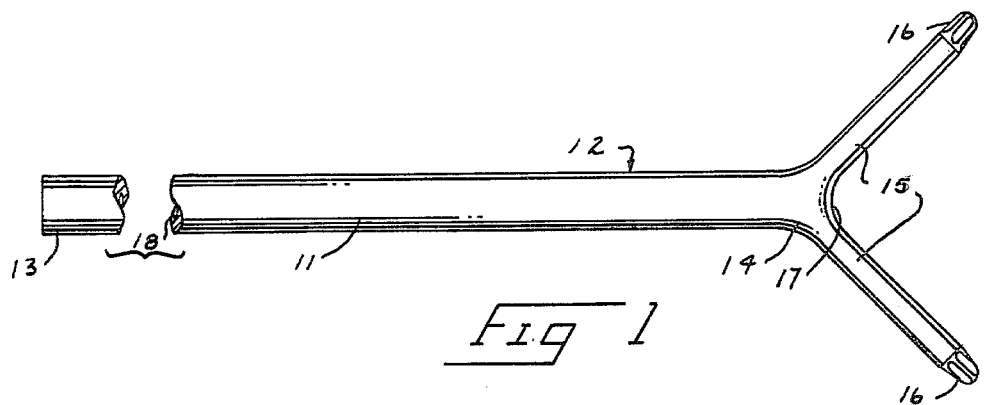
FIG. 1 is a fragmentary view illustrating the present bifurcated cannula.
Figure 2:
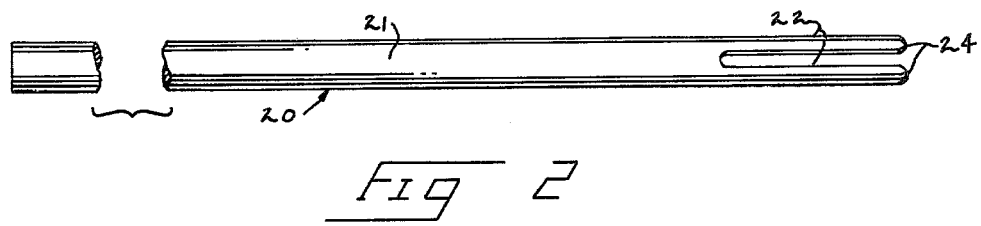
FIG. 2 is a fragmented view of an obtuator for insertion into the cannula of FIG. 1.

The present cannula assembly consists generally of a venous drainage tube 12 and a straight obtuator 20. The assembly is intended for use in cannulation of the right atrium, connecting the superior vena cava (SVC) and inferior vena cava (IVC) to the phlebotomy line of a conventional extracorporeal heart-lung system for cardiovascular bypass.

The present drainage cannula tube includes an elongated, preferably cylindrical hollow body 11 having an open outside end 13 leading inwardly on a constant diameter to a bifurcated inside end 14. The bifurcated end 14 is characterized by a pair of preferably cylindrical branches 15 that lead from a crotch 17 to blunt apertured tips 16 at free open tube ends. Each branch may have a constant diameter equal to no more than one half of the outside diameter of the tube body. The branches are shown to be equal in length. However, in some applications it may be desirable to have one branch longer than the other.

The tube body 11 includes a constant inside diameter lumen 18. The lumen 18 is formed along a central longitudinal axis of the tube body 11 and leads into integral smaller bore lumen 19 formed through the branches 15.

The obtuator 20 is formed of an elongated straight body 21 being bifurcated at an inward end. The inward end includes two straight branches 22 that are coextensive with the straight body 21. The branches 22 lead to rounded tips 24 to be received within the lumen 19 of the respective tube branches 15. The branches 22 are if sufficient length to extend the full length of the respective tube branches.

The obtuator body 21 is preferably cylindrical and of a diameter slightly less than that of the lumen 18. Similarly, the branches 22 are preferably circular in cross section, with diameters slightly smaller than the interior diameter of the branch lumina 19 of the tube 12. The obtuator therefore corresponds in cross section to the lumina 18 and 19, and is slidably receivable within the tube as illustrated in FIG. 3.

Figure 8:
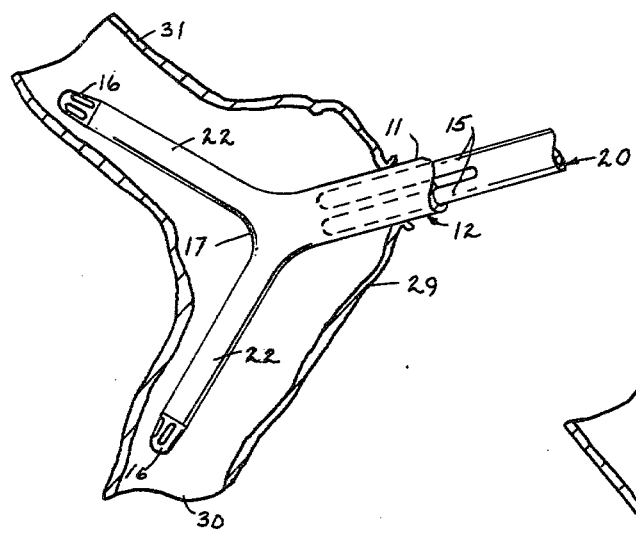
FIG. 8 is a diagrammatic view showing the cannula fully inserted.

The material forming the tube is preferably a synthetic resin of the vinyl family having resilient characteristics that will enable the branches to normally diverge (FIGS. 1 and 8) from the central longitudinal axis of the tubular body 11.

Figure 3:
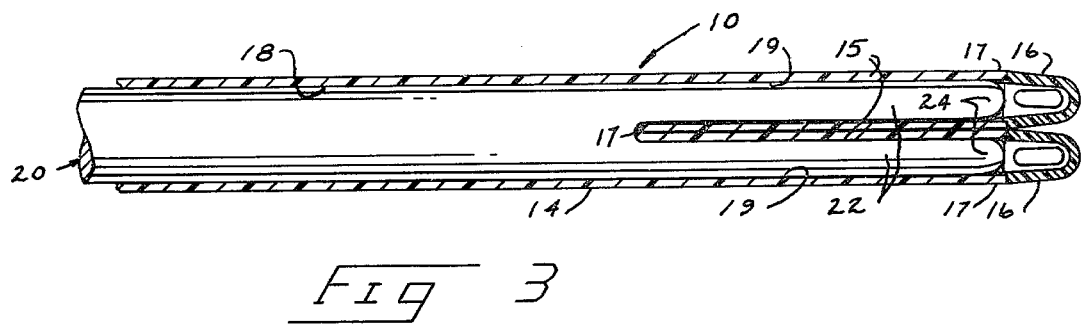
FIG. 3 is an enlarged sectional view illustrating placement of the obtuator within the cannula and resulting positions of the cannula branches.

The resilient branches can be straightened as shown in FIG. 3 to coextend with the tube body 11, (along the central axis) but when released as shown in FIG. 1, will return to the normal diverging angular relationship.

Figure 5:
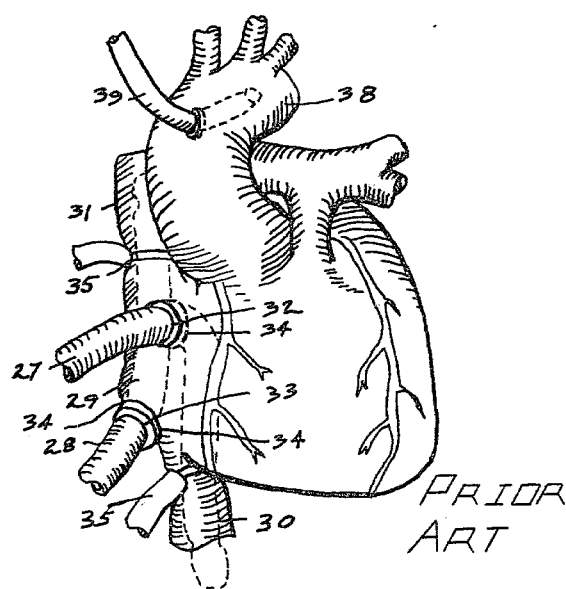
FIG. 5 is a diagrammatic illustration of the same technique only utilizing a prior art form of double cannula arrangement.

In order to appreciate the features and advantages of the present assembly during use, a brief description of prior cannulation apparatus and techniques is in order. FIG. 5 is illustrative of the conventional form of double cannulation apparatus. It includes an IVC cannula 27 and an independent SVC cannula 28. Cannula 27 is inserted through the walls of the atrium 29 into the IVC 30. Cannular 28 is inserted through a separate incision and directed upwardly into the SVC 31.

The IVC cannula 27 is inserted through an incision made in the appendix of the atrium. The incision is shown at 32 after insertion of the cannula 27. A second incision 33 is made through the wall of the atrium adjacent the inferior covatrial junction. Both cannulas 27 and 28 are secured to the tissue adjacent the incisions by snare sutures 34. Clamps or "tapes" 35 may be positioned on the SVC and IVC if isolation of the right atrium is desired.

Both cannulas 27 and 28 provide venous drainage from an extracorporeal heart-lung system (not shown). The cannulas 27 and 28 typically lead to a "Y" junction of a phlebotomy tube (also not shown). Blood is fed from the heart-lung machine through the cannulas 27 and 28 back into the patient's circulatory system. An aortic infusion cannula 39 is usually employed for directing blood to the extracorporeal heart-lung apparatus.

The surgical process for inserting the cannulas 27 and 28 involves clamping of the atrium wall to isolate the incision area from the cavity of the atrium. The snare suture 34 may then be placed about the area in which the incision is to be made. The incision is then made through the wall of the atrium in the clamped area. The cannula is quickly inserted following removal of the clamp and the snare suture is secured to prevent bleeding between the incision and cannula walls. These steps must be repeated for both cannulation sites.

Figure 4:
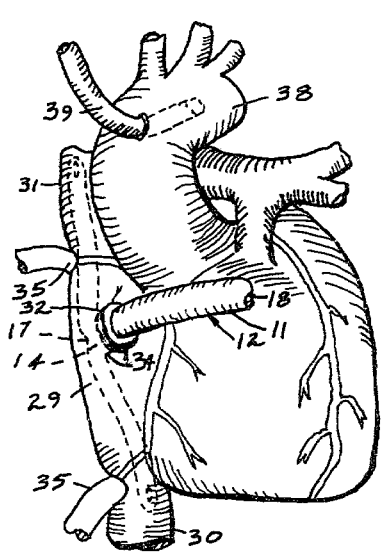
FIG. 4 is a diagrammatic view illustrating placement of the present cannula within the right atrium of a heart.

FIG. 4 illustrates a heart with the present cannula assembly being used for venous drainage. The bifurcated inside end of the present tube facilitates use of a single incision 32 preferably at the appendix of the atrium. FIGS. 6 through 9 diagrammatically illustrate the preferred method of insertion and removal of the cannula.

The cannula assembly is first prepared as shown in FIG. 3 with the obtuator 20 slidably received along the length of the tube to force the branches 15 against one another so they coextend with the tube body 11 along the longitudinal tube axis. The cross-sectional area occupied by the now parallel branches 15 is preferably slightly less than the cross-sectional area of the tube body 11.

The usual preparations are made for insertion of the cannula. The clamp is secured to the appendix and the usual snare suture is made. The incision is made to a length slightly greater than one half of the tube circumference.

Figure 6:
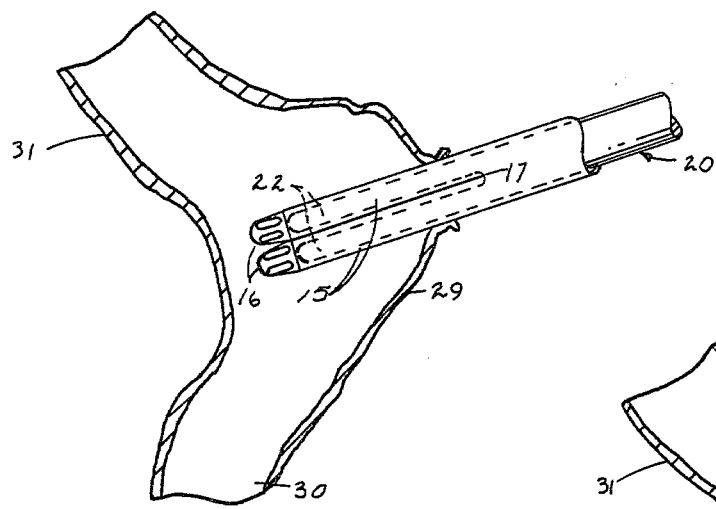
FIG. 6 is a diagrammatic view illustrating insertion of the present cannula assembly into the right atrium.

After the incision has been made, the clamp is released and the blunt tips 16 of the branches 15 are inserted into the cavity of the atrium. The snare sutures 34 can then be tightened slightly to prevent bleeding from around the two straightened branches 15. Relative position of the tube 12, obtuator 20, and cavae 30, 31 are shown in FIG. 6.

Figure 7:
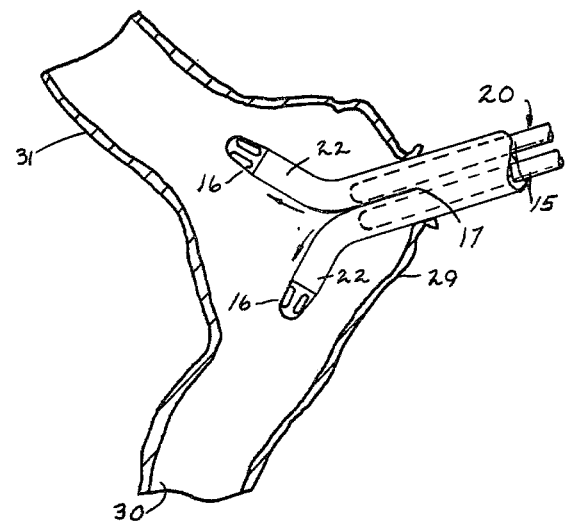
FIG. 7 is a view illustrating a subsequent step of guiding the cannula branches into the atrium following insertion.

Subsequent to insertion, the surgeon may hold the obtuator 20 stationary with one hand while urging the tube 12 inwardly with the other. The tube will slide inwardly with the branches becoming disengaged from the rounded tips 24 of the obtuator branches. The resilient branches will automatically return to their diverging positions, seeking entrance through the cavoatrial junctions of the respective IVC and SVC. This motion is illustrated in FIG. 7.

The branches 15 are of sufficient length so upon full insertion, (FIG. 8) each tube branch will extend a desired distance into the lumen of the superior and inferior vena cavae with the crotch 17 situated within the cavity of the atrium. Therefore, only the single tube body 11 protrudes through the appendicular incision. If necessary, the branch ends 17 may be clamped (FIG. 4) selectively to the respective cavae by appropriate clamps or tapes 35.

Figure 9:
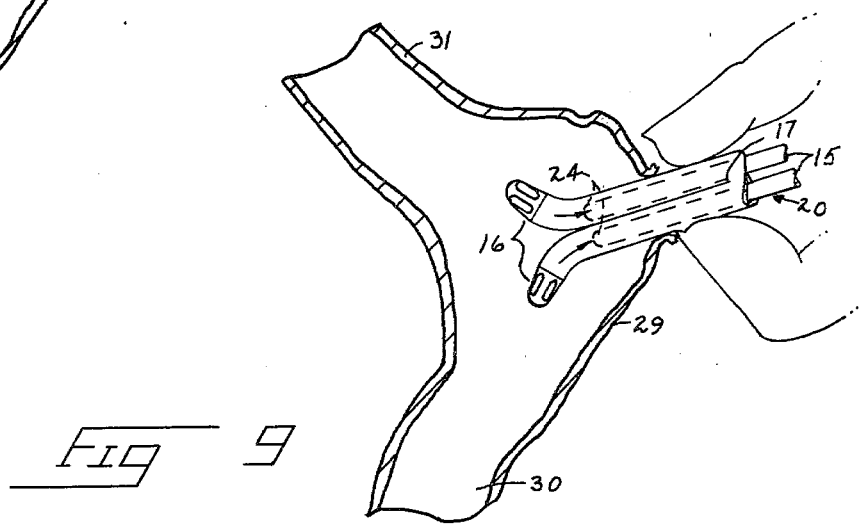
FIG. 9 is a similar diagrammatic view only showing retraction of the cannula through the single incision.

Removal of the cannula is accomplished after separation of the cannula end 13 from the heart-lung phlebotomy line. The tube is held normal to the chest cavity, preferably at an upright orientation. The obtuator is then inserted along the tube lumina until the rounded tips 24 project into the cavity of the atrium at the position of the tube crotch 17 (FIG. 9). The obtuator is then held stationary while the tube is retracted. The obtuator branches 22 contact the walls of the tube branches 15, camming them together gradually as they are withdrawn. There is therefore little if any strain placed upon tissue in the area of the incision. Closing is accomplished in the usual manner following full retraction of the cannula.

Distinct advantages of the present cannula assembly and its use become evident from comparing the prior art arrangement shown by FIG. 5 with the present arrangement shown in FIG. 4. Obviously, a single venous drainage line extending from the atrium presents substantially less obstruction to the surgeon than the prior double cannula arrangement. With easier access comes shorter overall operation time. Furthermore, the danger from complications arising from the cannulation incisions is cut by one half since only one incision is required. The time required to insert and remove the cannulas is also greatly reduced.

The above description and attached drawings are given by way of example to set forth a preferred form of the present invention. Other forms may be envisioned which fall within the scope of my invention. Therefore, the scope of the present invention is set forth more precisely in the following claims.

What I claim is:

1. A venous drainage cannula assembly for insertion into the superior and inferior vena cavae through a single incision in the right atrium, comprising:

an elongated resilient tube including a hollow body leading from an open outward end along a longitudinal axis, inwardly to an integral bifurcated tube end, the bifurcations forming two branches joining integrally with the hollow body at a crotch section of the tube;

wherein the branches extend from the crotch to free open ends, with the length of the branches from the crotch to the free ends being sufficient to allow positioning of the free open ends within the superior and inferior vena cavae with the crotch situated within the right atrium and the incision edges engaging the hollow body toward the open outward tube end from the crotch;

wherein the branches normally diverge from the crotch to the free tube ends, forming a "Y" configuration with the hollow tube body; and rigid obturator means having an elongated shaft slidably receivable within the length of the resilient tube and with straight extensions integral and coextensive with the shaft having a rounded end to be (a) received within the tube branches so the tube branches may be straightened by the rounded extension ends to extend parallel to the axis of the tube body as the obturator is inserted and moved relative to the tube toward the bifurcated end, and (b) allow the tube branches to spread back against the rounded extension ends to their normal diverging positions, all within the right atrium, thereby avoiding trauma to tissues at the incision upon insertion and withdrawal of the cannula.

2. The cannula assembly as defined by claim 1 wherein:

the tube and branches thereof are cylindrical and the open outward end of the tube includes an outside diameter at least equal to the sum of corresponding outside diameters of the tube branches at the bifurcated end.

3. The assembly as defined by claim 1 wherein the tube branches when drawn together along the longitudinal axis present a cross-sectional dimension not greater than the outside cross-sectional dimension of the tube at its outward end.

4. A process for cannulating the superior and inferior vena cavae through the right atrium using a venous drainage cannula formed of a hollow elongated resilient tube having a bifurcated end with resilient tube branches thereof normally diverging to free ends from an integral crotch to form a "Y" configuration, said cannula slidably receiving an elongated rigid internal obturator having parallel axial obturator branches at an end thereof extending to branch ends receivable within the cannula tube and tube branches to selectively cam the tube branches together and apart in response to relative axial motion of the tube and obturator, wherein the process includes the steps of:

forming a snare suture along a selected area of the atrium within the area encompassed by the snare suture;

inserting the free tube ends and obturator ends into the atrium through the incision, with the tube branches held together by the obturator branches until the obturator branch ends project into the atrium;

holding the obturator axially stationary with its branch ends within the atrium;

simultaneously continuing insertion of the cannula so the resilient cannula branches will progressively diverge from the obturator branch ends until the cannula crotch is located within the atrium and the tube branches extend into the superior and inferior vena cavae;

tightening the snare suture about the tube; and removing the obturator from the cannula.

5. The process as claimed by claim 4 including the further steps for removing the cannula from the atrium by:

inserting the obturator axially into the cannula until the obturator branch ends project into the atrium and into the cannula branches at the crotch;

loosening the snare suture;

holding the obturator axially stationary;

withdrawing the cannula over the axially stationary obturator so the tube branches cam together against the obturator branch ends within the atrium until the tube branches are parallel with the tube and the free tube branch ends are adjacent the obturator branch ends;

withdrawing the obturator and cannula branch ends from the atrium; and closing the incision.

6. The process as claimed by claim 4 comprising the further step of tightening the snare suture about the tube branches immediately following their insertion through the incision to minimize bleeding between the incision and the tube branches.

* * * * *